United States Patent [19]

Feder

[11] Patent Number: 5,046,200

[45] Date of Patent: Sep. 10, 1991

[54] REVERSIBLE, QUICK-ADJUSTABLE DIVER'S FACE MASK STRAP

[76] Inventor: Irving Feder, 331 Poinciana Island Dr., Miami Beach, Fla. 33160

[21] Appl. No.: 575,374

[22] Filed: Aug. 29, 1990

[51] Int. Cl.$^5$ .............................. A61F 9/02; G02C 3/00
[52] U.S. Cl. ...................................... 2/452; 351/156; 128/207.11
[58] Field of Search ................ 2/452, 428, 429, 430; 128/200.28, 201.22, 207.11, 207.17; 351/43, 156

[56] References Cited

U.S. PATENT DOCUMENTS

| | | | |
|---|---|---|---|
| 1,023,285 | 4/1912 | White | 2/9 |
| 1,942,442 | 12/1931 | Motsinger | 128/140 |
| 2,928,097 | 3/1960 | Neufeld | 2/430 |
| 2,974,665 | 2/1954 | Motsinger | 128/141 |
| 3,605,204 | 9/1971 | Amundsen | 2/452 |
| 3,606,648 | 9/1971 | Schuler | 2/452 |
| 3,768,100 | 10/1973 | Colman et al. | 2/9 |
| 4,066,077 | 1/1978 | Shamliau | 128/145 R |
| 4,112,521 | 9/1978 | Uke | 2/452 |
| 4,264,987 | 5/1981 | Runckel | 2/452 |
| 4,520,509 | 6/1985 | Ward | 2/206 |
| 4,520,813 | 6/1985 | Young | 128/207.17 |
| 4,534,344 | 8/1985 | Constance-Hughes | 128/201.15 |
| 4,562,836 | 1/1986 | Perrou | 128/201.11 |
| 4,564,960 | 1/1986 | Nishiyama | 2/452 |
| 4,595,003 | 6/1986 | Shoemaker et al. | 128/201.19 |
| 4,607,398 | 8/1986 | Faulconer | 2/452 |
| 4,692,002 | 9/1987 | Meistrell | 351/156 |
| 4,779,291 | 10/1988 | Russell | 351/43 |
| 4,910,806 | 3/1990 | Baker et al. | 2/452 |

FOREIGN PATENT DOCUMENTS

| | | | |
|---|---|---|---|
| 987989 | 8/1951 | France | 2/428 |
| 1095781 | 12/1954 | France | 128/207.11 |
| 90/00380 | 1/1990 | PCT Int'l Appl. | 2/430 |

*Primary Examiner*—Werner H. Schroeder
*Assistant Examiner*—Michael A. Neas
*Attorney, Agent, or Firm*—Herbert L. Lerner; Laurence A. Greenberg

[57] ABSTRACT

A reversible, quick-adjustable diver's face mask strap includes a body portion formed of a flexible, elastic material having first and second opposite surfaces for contacting the head of a diver. The body portion includes two band portions being partially spaced apart defining an opening therebetween. The strap further includes first and second ribbons attached to the body portion, each of the ribbons having an attachment surface and another surface. Each of the other surfaces are connected to a respective one of the opposite first and second surfaces. Each of the ribbons have fasteners disposed on the attachment surface for releasably fastening the attachment surface to itself when folded to form a loop passing through an opening formed in a diver's face mask. One of the ribbons thereby remains adjustable without removing the mask strap from the diver's head regardless of which one of the opposite surfaces contacts the head of the diver.

10 Claims, 3 Drawing Sheets

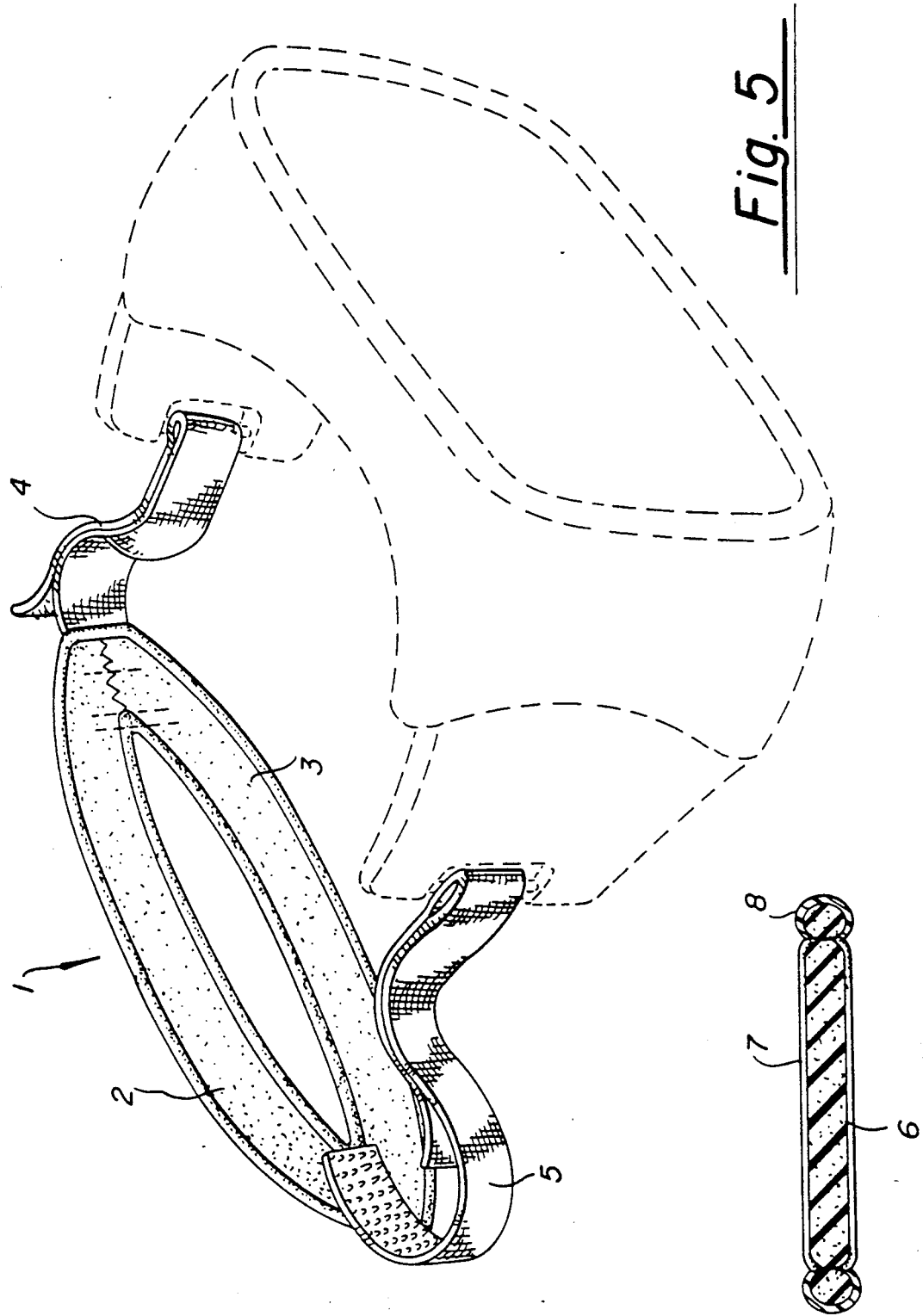

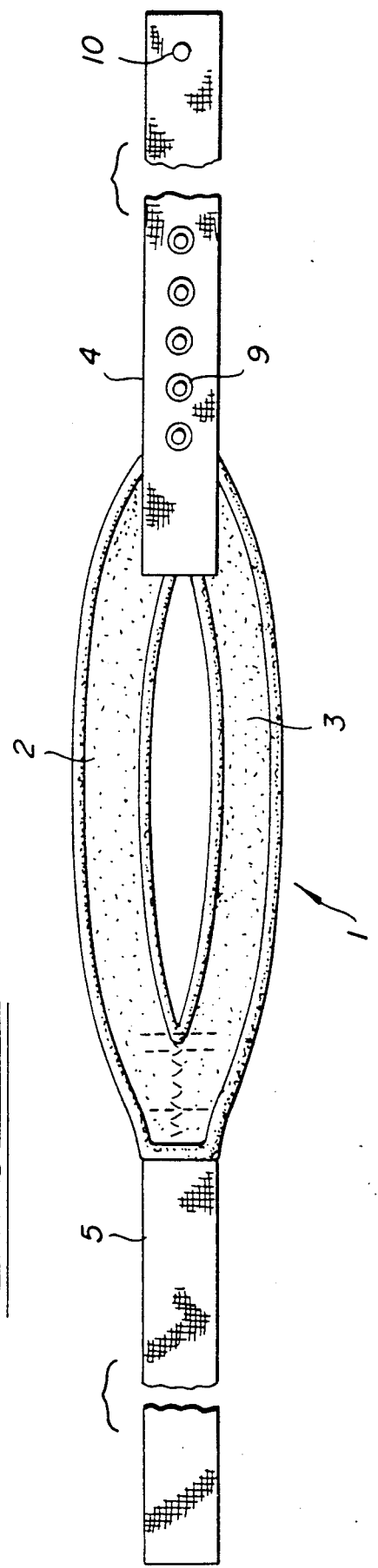
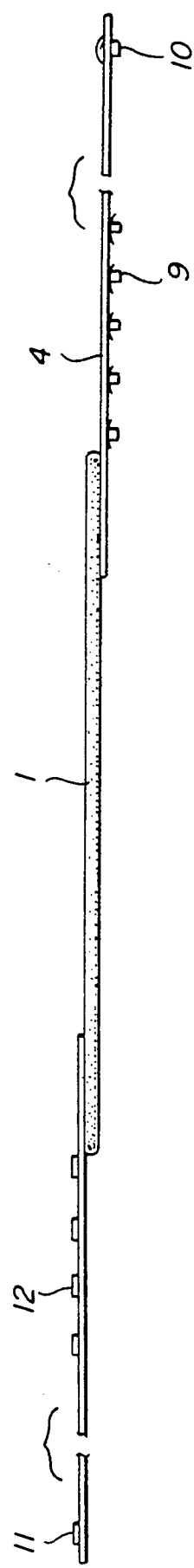
Fig. 7
Fig. 8

REVERSIBLE, QUICK-ADJUSTABLE DIVER'S FACE MASK STRAP

BACKGROUND OF THE INVENTION

1. Field of the Invention

The invention relates to a face mask strap, in particular a reversible, quick-adjustable diver's face mask strap which allows for quick and easy readjustment of the mask strap even under water without having to move the mask or release it from sealing against the diver's face.

2. Description of the Prior Art

It has become known in the recent past to replace the older rubber-type mask straps with more convenient fabric-laminated, soft headbands. This new generation of mask straps is gentler to the back of the wearer's head and the tangling of hair is largely avoided. However, the mask strap is not as securely seated on the back of the diver's head as in the case of the old rubber straps.

It has further become known to use quick-adjustable straps such as the one disclosed in U.S. Pat. No. 4,112,521 to Uke.

Soft fabric-laminated mask straps, such as the one disclosed in U.S. Pat. No. 4,910,806 to Baker et al., while offering some advantages over the old rubber straps, have also shown some disadvantageous features. For instance, the soft hook-type fastening material on the inner surface of the strap wears out during extended use, and the connection thereby becomes weaker.

Furthermore, the advantage of avoiding the tangling of hair by using fabrics on the top of the strap to contact the diver's head entails the disadvantage that the strap is not as well positioned on the diver's head as the old rubber-type strap, with its much higher coefficient of friction. Also, the fabric-laminated mask strap is not very suitable for use by a hooded diver, since the strap slides rather easily out of a convenient and secure position on the back of the diver's head.

Yet another problem encountered in using the soft materials for the strap is that while the diver descends into deeper waters the pressure increases. This causes the strap materials such as foam or neoprene to expand and the mask to loose its tight fit on the diver's head. Accordingly, the diver's mask strap must be readjusted quickly when the water pressure increases.

SUMMARY OF THE INVENTION

It is accordingly an object of the invention to provide a reversible, quick-adjustable diver's face mask strap, which overcomes the hereinafore-mentioned disadvantages of the heretofore-known devices of this general type, which makes it possible to adjust the tension on the mask strap under water, which is suitable for use by hooded as well as non-hooded divers, and which can be securely placed on the diver's head by independently adjusting two band portions to best conform with the shape of the diver's head.

With the foregoing and other objects in view there is provided, in accordance with the invention, a reversible, quick-adjustable diver's face mask strap, comprising a body portion formed of a flexible, elastic material having first and second opposite surfaces for contacting the head of a diver, the body portion including two band portions being partially spaced apart defining an opening therebetween, first and second ribbons attached to the body portion, each of the ribbons having an attachment surface and another surface, each of the other surfaces being connected to a respective one of the opposite first and second surfaces, each of the ribbons having means disposed on the attachment surface for releasably fastening the attachment surface to itself when folded to form a loop passing through an opening formed in a diver's face mask, whereby one of the ribbons remains adjustable without removing the mask strap from the diver's head regardless of which one of the opposite surfaces contacts the head of the diver.

In accordance with another feature of the invention, the fastening means are hook-and-eye type fasteners. Modern construction of these fasteners, such as VELCRO, allow repeated use under water without wear. However, in accordance with a further feature of the invention, the fastening means are in the form of snaps or clips.

In accordance with an added feature of the invention, the body portion is formed of a closed-cell elastomeric material.

In accordance with still a further feature of the invention, the elastomeric material is laminated with fabric on at least one side thereof. When the strap is laminated with a fabric with a low coefficient of friction on one side and having a high coefficient of friction on the other side, the mask strap can be used by a diver who sometimes uses a hood and sometimes does not.

In accordance with an additional feature of the invention, the body portion is formed of neoprene or Darlexx brand material laminated with fabric.

In accordance with again further features of the invention, the fabric is formed of nylon, polyester or Lycra.

In accordance with a concomitant feature of the invention, the fabric is formed of a stretchable material.

Other features which are considered as characteristic for the invention are set forth in the appended claims.

Although the invention is illustrated and described herein as embodied in a reversible, adjustable diver's face mask strap, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE DRAWINGS

FIG. 5 is a perspective view of the strap according to the invention attached to a diver's face mask;

FIG. 6 is a cross-sectional view taken along the line VI—VI of FIG. 1, in the direction of the arrow;

FIG. 7 is a view similar to that of FIG. 1, showing a second embodiment of the invention; and FIG. 8 is a view similar to FIG. 3, showing the second the third embodiments of FIG. 7.

DESCRIPTION OF THE PREFERRED EMBODIMENTS

Figure 1:
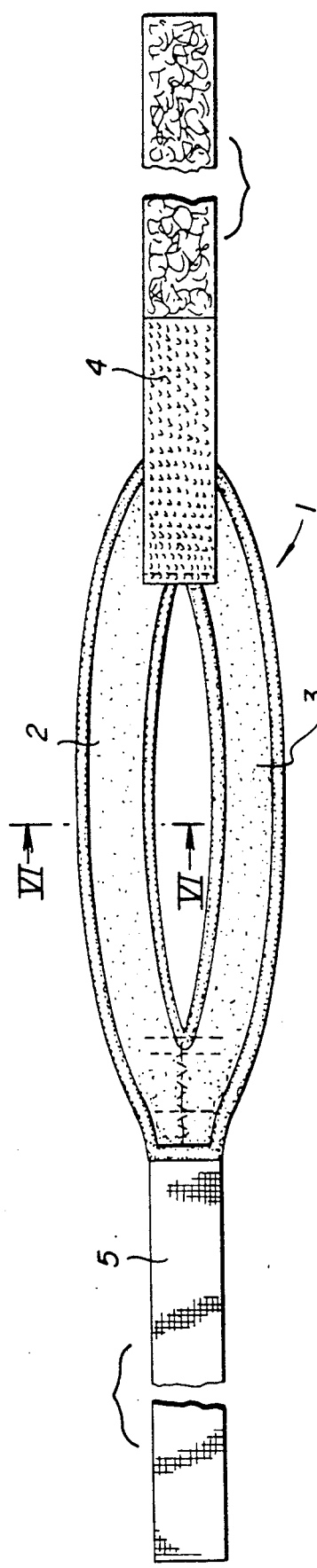
FIG. 1 is a fragmentary side-elevational view of the diver's mask strap according to the invention.
Figure 2:
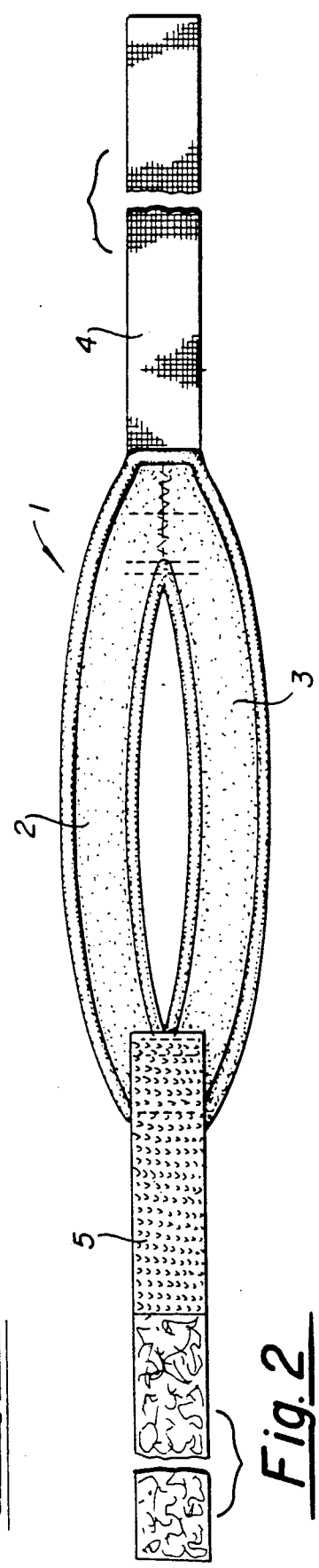
FIG. 2 is a view similar to FIG. 1 showing the reverse side of the strap shown therein.

Referring now to the figures of the drawing in detail and first, particularly, to FIGS. 1 and 2 thereof, there is seen a body portion 1 of a diver's mask strap. The body portion 1 is made of stretchable materials, such as Darlexx or neoprene covered with Lycra, nylon or a polyester fabric. The body portion 1 is made up of two band portions 2 and 3, forming an opening therebetween.

The two band portions 2 and 3, to a degree, are independently adjustable, so that they can be made to conveniently conform to the shape of the back of the diver's head. It has also been found that the mask strap with two band portions 2 and 3 is more stable on the diver's head than a single surface strap.

Attached to the body portion 1 are two ribbons 4 and 5. In comparing FIGS. 1 and 2, it can be seen that the ribbon 4 extends onto one surface of the body portion 1 while the ribbon 5 extends onto the opposite surface. The mask strap of the invention of the instant application is thus reversible.

The ribbons 4 and 5 are covered with a hook-and-eye type fastener such as "VELCRO". The distal ends of the ribbons 4 and 5 fold back onto their respective proximal ends, thus forming a loop for attaching a diver's mask. It is also possible to use snaps or clips instead of the hook-and-eye type fastener.

The distal ends of the ribbons 4 and 5, as shown in the drawings, carry loops or eyes, and the proximal ends which extend onto the body portion 1 carry the hooks. This construction, however, can be reversed.

Figure 3:
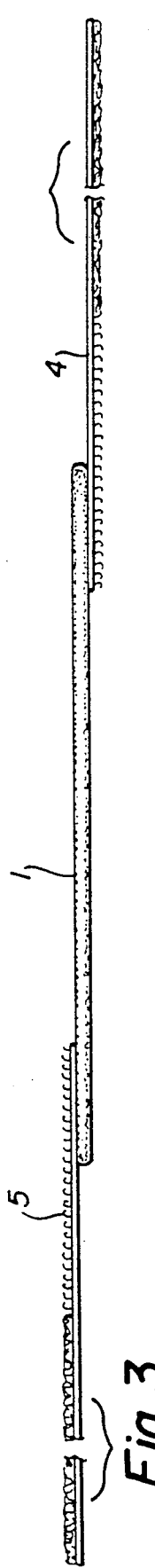
FIG. 3 is a top-plan view of the strap according to the invention.
Figure 4:
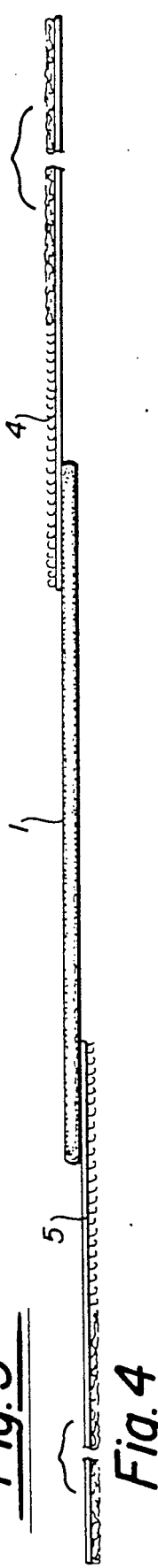
FIG. 4 is a bottom-plan view of the strap.

As more clearly illustrated in FIGS. 3 and 4, the ribbons 4 and 5 are attached to opposite surfaces of the body portion 1. Thus, in order to close the ribbons 4 and 5, for example in FIG. 3, both ribbons 4 and 5 are folded back onto themselves in a clockwise direction, while in the view shown in FIG. 4 both ribbons 4 and 5 are folded back onto themselves in a counter-clockwise direction.

It is thus seen in FIGS. 3 and 4 that the ribbon members 4 and 5 each have a smooth surface and an attachment surface, the latter carrying the hook-and-eye type fastener.

As seen in FIG. 5, wherein the mask strap of the invention is attached to a diver's mask shown in broken lines, the ribbon 5 is folded back on the inside. The ribbon 4, however, is folded back on the outside, and it can thus be adjusted without removing the diver's mask. The ribbon 4, and thus the tension on the mask strap can therefore be quickly adjusted even under water without loosing the sealing effect of the mask.

It has further been found that, when the underwater pressure increases as the diver descends into deeper waters, the elastic materials such as neoprene are compressed and the strap is extended. Easy and quick readjustment of the mask strap is therefore possible with the strap according to the invention.

It can be easily seen that, when the mask strap is reversed, the ribbon 4 will fold back on the inside and the ribbon 5 will be the quick-adjust ribbon, whose distal end is then accessible to the diver's hand while the distal end of the ribbon 4 is disposed between the proximal end of the ribbon 4 and the diver's head.

As illustrated in FIG. 6, the body portion 1, and thus the bands 2 and 3 are made from a base material 6 covered with an elastic fabric 7. The base material 6 is a closed-cell elastomeric material such as neoprene (manufactured, for example, by Rubatex, Bedford, Virginia) or Darlexx (manufactured, for example, by Darlington Industries, New York, N.Y); these materials come in various densities and stretch coefficients.

The base 6 is laminated with an outer layer of an elastic fabric 7. Although largely decorative in nature, the fabric 7 fulfills an additional function in that it reinforces the base material 6. Furthermore, a hooded diver may prefer to use a side of the strap to contact the hood on the back of his head which is not laminated or laminated with a fabric which has a high coefficient of friction. A further advantage of the strap of the instant invention is thus seen in that it is suitable for use by divers with or without hoods.

The fabric 7 may be nylon, Lycra, polyester, or any other material that, preferably, does not engage with VELCRO. Different color fabrics are used for the opposite surfaces of the body, so that, since the mask strap of the invention is fully reversible, different colors or design patterns can be displayed by the diver wearing the mask.

The embodiment illustrated in the drawings is shown with an over-edge stitch or hem stitch 8. Various other edge stitches are possible, however. It has been found that it is also possible to merely cut the base material 6 laminated with the fabric 7 without any further decorative edge treatment or edge stitching.

As shown in FIGS. 7 and 8, the ribbons 4 and 5 may be fastened with snaps 9 and 10 or with clips 11 and 12.

I claim:

1. A reversible, quick-adjustable diver's face mask strap, comprising a body portion formed of a flexible, elastic material having first and second opposite surfaces for contacting the head of a diver, said body portion including two band portions being partially spaced apart defining an opening therebetween, first and second ribbons attached to said body portion, each of said ribbons having an attachment surface and another surface, each of said other surfaces being connected to a respective one of said opposite first and second surfaces, each of said ribbons having means disposed on said attachment surface for releasably fastening said attachment surface to itself when folded to form a loop passing through an opening formed in a diver's face mask, whereby one of said ribbons remains adjustable without removing the mask strap from the diver's head regardless of which one of said opposite surfaces contacts the head of the diver.

2. The mask strap according to claim 1, wherein said fastening means are hook-and-eye type fasteners.

3. The mask strap according to claim 1, wherein said fastening means are snaps.

4. The mask strap according to claim 1, wherein said fastening means are clips.

5. The mask strap according to claim 1, wherein said elastic material is a closed-cell elastomeric material.

6. The mask strap according to claim 5, wherein said elastomeric material is laminated with fabric on at least one of said opposite surfaces.

7. The mask strap according to claim 1, wherein said body portion is formed of neoprene laminated with fabric.

8. The mask strap according to claim 6, wherein said fabric is nylon.

9. The mask strap according to claim 6, wherein said fabric is a polyester.

10. The mask strap according to claim 6, wherein said fabric is formed of a stretchable material.

* * * * *